United States Patent
Horikiri et al.

(10) Patent No.: US 9,115,055 B2
(45) Date of Patent: Aug. 25, 2015

(54) FLUORENYLAMINE COMPOUND, ORGANIC LIGHT EMITTING DEVICE CONTAINING THE SAME, MATERIAL FOR ORGANIC LIGHT EMITTING DEVICE, DISPLAY APPARATUS, AND IMAGE INPUT APPARATUS

(75) Inventors: Tomonari Horikiri, Sagamihara (JP); Naoki Yamada, Inagi (JP); Maki Okajima, Kawasaki (JP); Minako Nakasu, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 576 days.

(21) Appl. No.: 13/503,989

(22) PCT Filed: Oct. 18, 2010

(86) PCT No.: PCT/JP2010/006153
§ 371 (c)(1),
(2), (4) Date: Apr. 25, 2012

(87) PCT Pub. No.: WO2011/055493
PCT Pub. Date: May 12, 2011

(65) Prior Publication Data
US 2012/0211742 A1    Aug. 23, 2012

(30) Foreign Application Priority Data
Nov. 5, 2009 (JP) ................... 2009-254006

(51) Int. Cl.
H01L 51/50 (2006.01)
C07C 211/61 (2006.01)
C09K 11/06 (2006.01)
H01L 51/00 (2006.01)

(52) U.S. Cl.
CPC .............. C07C 211/61 (2013.01); C09K 11/06 (2013.01); H01L 51/006 (2013.01); H01L 51/5016 (2013.01); *C07C 2103/18* (2013.01); *C09K 2211/1011* (2013.01)

(58) Field of Classification Search
None
See application file for complete search history.

(56) References Cited

U.S. PATENT DOCUMENTS

| | | | | |
|---|---|---|---|---|
| 2004/0170863 A1* | 9/2004 | Kim et al. | ...... | 428/690 |
| 2005/0123790 A1* | 6/2005 | Royster et al. | ...... | 428/690 |
| 2007/0018569 A1* | 1/2007 | Kawamura et al. | ...... | 313/504 |
| 2007/0290213 A1* | 12/2007 | Kobayashi | ...... | 257/79 |
| 2010/0002148 A1* | 1/2010 | Otawara et al. | ...... | 348/678 |
| 2010/0033081 A1* | 2/2010 | Yamada et al. | ...... | 313/504 |

FOREIGN PATENT DOCUMENTS

| | | | |
|---|---|---|---|
| JP | 3-78756 A | 4/1991 | |
| JP | 11-184109 A | 7/1999 | |
| JP | 2007-311759 A | 11/2007 | |
| JP | 2008-297535 A | 12/2008 | |
| WO | WO 2007123259 | * 1/2007 | ...... C09K 11/06 |

* cited by examiner

*Primary Examiner* — Gregory Clark
(74) *Attorney, Agent, or Firm* — Canon USA Inc. IP Division

(57) ABSTRACT

A novel fluorenylamine compound represented by a general formula below, where $R_1$ to $R_6$ are each independently selected from a hydrogen atom and alkyl groups; $R_{21}$ to $R_{23}$ are each independently selected from a hydrogen atom and the alkyl groups; and the alkyl groups are a methyl group, an ethyl group, a n-propyl group, an isopropyl group, a n-butyl group, an isobutyl group, a sec-butyl group, and a tert-butyl group.

[Chem. 2]

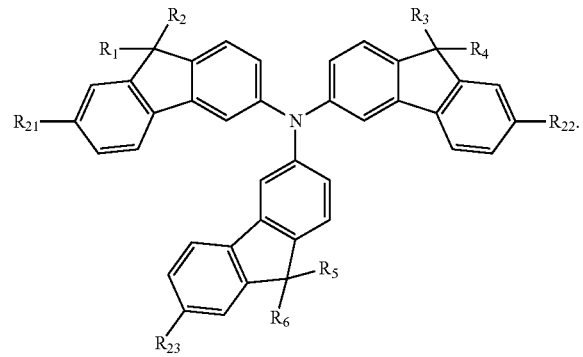

11 Claims, 1 Drawing Sheet

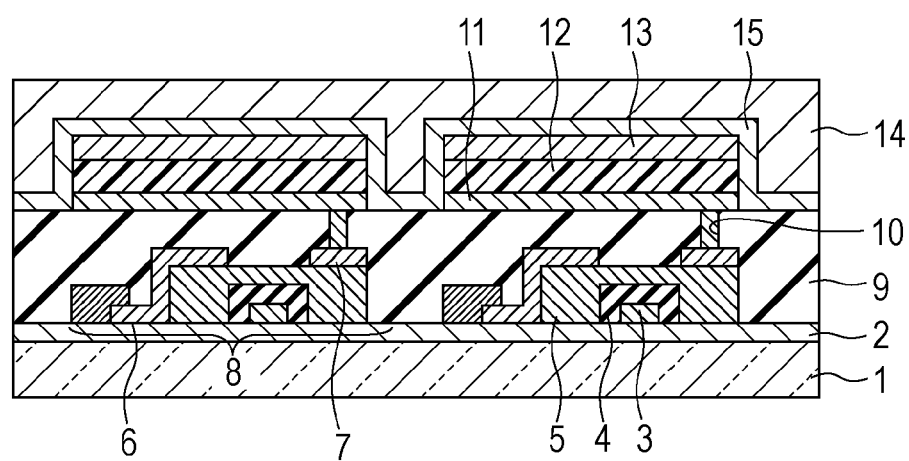

FLUORENYLAMINE COMPOUND, ORGANIC LIGHT EMITTING DEVICE CONTAINING THE SAME, MATERIAL FOR ORGANIC LIGHT EMITTING DEVICE, DISPLAY APPARATUS, AND IMAGE INPUT APPARATUS

TECHNICAL FIELD

The present invention relates to a novel fluorenylamine compound, a material for an organic light emitting device, an organic light emitting device containing such a novel fluorenylamine compound, a display apparatus including such an organic light emitting device, and an image input apparatus including such an organic light emitting device.

BACKGROUND ART

An organic light emitting device includes a positive electrode, a negative electrode, and an organic compound layer disposed between the positive electrode and the negative electrode.

An organic compound used for such an organic light emitting device is required to have thermal stability. This is because functions of the organic compound are degraded by heat.

Patent Literature 1 describes, as a compound having a high thermal stability, a compound illustrated as Compound 1 below.

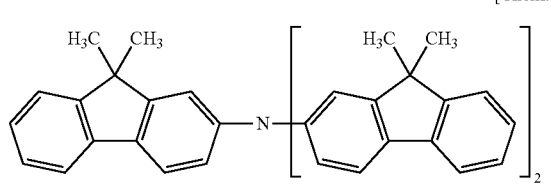

[Chem.1]

CITATION LIST

Patent Literature

PTL 1: Japanese Patent Laid-Open No. 11-184109 (no publication outside Japan)

SUMMARY OF INVENTION

Compound 1, which is a compound described in Patent Literature 1, does not have a sufficiently large band gap and does not have a sufficiently high lowest excited triplet level.

The present invention provides an organic compound that has a high thermal stability, a large band gap, and a high lowest excited triplet level.

Accordingly, the present invention provides a fluorenylamine compound represented by a general formula below,

[Chem.2]

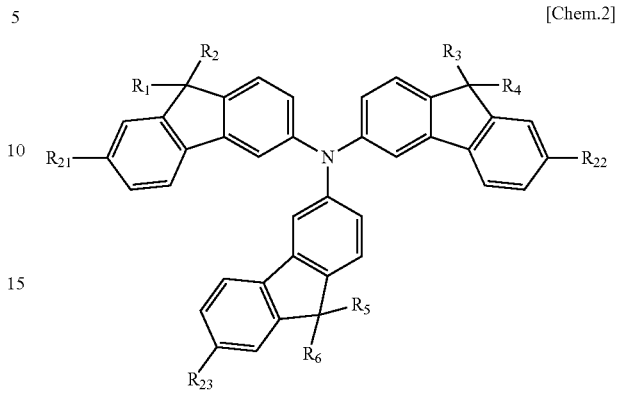

In this general formula, $R_1$ to $R_6$ are each independently selected from a hydrogen atom and alkyl groups; $R_{21}$ to $R_{23}$ are each independently selected from a hydrogen atom and the alkyl groups.

The alkyl groups are a methyl group, an ethyl group, a n-propyl group, an isopropyl group, a n-butyl group, an isobutyl group, a sec-butyl group, and a tert-butyl group.

The present invention can provide an organic compound that has a high glass transition temperature. In addition, this organic compound includes three fluorenyl groups bonded to a nitrogen atom at the 3-positions, and hence has a large band gap and a high lowest excited triplet level.

BRIEF DESCRIPTION OF DRAWINGS

FIG. 1 is a schematic sectional view illustrating organic light emitting devices and thin-film transistor (TFT) devices connected to the organic light emitting devices.

DESCRIPTION OF EMBODIMENTS

The present invention provides a novel fluorenylamine compound represented by the following general formula.

[Chem.3]

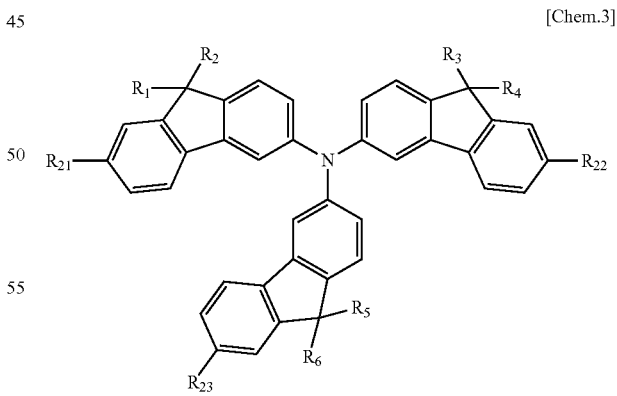

In this general formula, $R_1$ to $R_6$ are each independently selected from a hydrogen atom and alkyl groups. $R_{21}$ to $R_{23}$ are each independently selected from a hydrogen atom and the alkyl groups.

The alkyl groups are a methyl group, an ethyl group, a n-propyl group, an isopropyl group, a n-butyl group, an isobutyl group, a sec-butyl group, and a tert-butyl group.

A fluorenylamine compound according to the present invention is a compound including, as a main structure, a nitrogen atom and three fluorenyl groups bonded to the nitrogen atom at the 3-positions. $R_1$ to $R_6$, which are bonded to the main structure in the general formula, are each independently selected from a hydrogen atom and alkyl groups. $R_{21}$ to $R_{23}$, which are also bonded to the main structure in the general formula, are each independently selected from a hydrogen atom and alkyl groups.

Examples of alkyl groups that may be included in $R_1$ to $R_6$ and $R_{21}$ to $R_{23}$ include a methyl group, an ethyl group, a n-propyl group, an isopropyl group, a n-butyl group, an isobutyl group, a sec-butyl group, and a tert-butyl group.

Introduction of an alkyl group serving as a substituent into a fluorenyl group can decrease the ionization potential of the compound. This low ionization potential means that positive holes are readily injected from a positive electrode, which leads to the operation of an organic light emitting device at a low voltage. The low ionization potential means that the ionization potential is close to the vacuum level.

A fluorenylamine compound according to the present invention has a high glass transition temperature (Tg) and a high thermal stability. This is because all the three fluorenyl groups are bonded at the 3-positions.

Since the fluorenylamine compound includes three fluorenyl groups that are all bonded to a nitrogen atom at the 3-positions, compared with Compound 1 including fluorenyl groups that are bonded to a nitrogen atom at the 2-positions, the fluorenylamine compound has a low flatness in its entirety and a low probability of association between molecules. Thus, the fluorenylamine compound forms a stable amorphous film in which crystallization is less likely to occur.

In a fluorenylamine compound according to the present invention, since all the three fluorenyl groups are bonded to a nitrogen atom at the 3-positions, conjugation is not achieved in the entirety of the fluorene molecules but is locally achieved in portions where the fluorenyl groups are bonded to the nitrogen atom and near the portions. As a result, the fluorenylamine compound has a large band gap and a high lowest excited triplet level (T1). Table 1 below summarizes T1s measured in a toluene solution at −78 degree (Celsius).

TABLE 1

| Compound | T1 (eV) |
|---|---|
| Exemplified compound A1 | 2.72 |
| Compound 1 | 2.51 |
| Ir(ppy)3 | 2.49 |

Compared with the T1 of Compound 1, since the T1 of Exemplified compound A1 has a large difference from the T1 of Ir(ppy)3, which is a green phosphorescence emitting material, triplet excitons are less likely to move from a light emitting layer to a hole transport layer, which is adjacent to the light emitting layer. In contrast, since the T1 of Compound 1 is almost the same as that of the green phosphorescence emitting material, some triplet excitons probably move from a light emitting layer to a hole transport layer, which is adjacent to the light emitting layer. Thus, Exemplified compound A1 can be suitably used as a host material of a hole transport layer or a light emitting layer in a device containing the green phosphorescence emitting material.

A phosphorescence emitting material is a compound that emits phosphorescence at room temperature. A fluorescence emitting material is a compound that emits fluorescence at room temperature.

Here, among compounds forming a light emitting layer, a compound having the largest weight proportion is a host material and compounds having smaller weight proportions than the host material are guest materials.

Due to the above-described advantage, when a compound according to the present invention is used for a hole transport layer, singlet excitons and triplet excitons generated in a light emitting layer are contained in the light emitting layer and hence the efficiency is enhanced.

A fluorenylamine compound according to the present invention is also suitably used as a host material in a light emitting device including a light emitting layer containing the host material and a guest material. Since a fluorenylamine compound according to the present invention has a large band gap, such a fluorenylamine compound can be used as the host material of a light emitting layer containing a blue fluorescence emitting material requiring a large band gap. Thus, excitons generated in the host material can be moved to the guest material and the light can be efficiently emitted. Furthermore, a fluorenylamine compound according to the present invention may be used as the host material of a light emitting layer of an organic light emitting device containing a fluorescence emitting material that emits green light or red light.

Since a fluorenylamine compound according to the present invention has a high T1, the fluorenylamine compound can be suitably used as the host material of a light emitting layer containing a green fluorescence emitting material. This is because the fluorenylamine compound has a higher T1 than the green fluorescence emitting material. Accordingly, triplet excitons generated in the host material can be moved to the guest material and the light can be efficiently emitted. As for such a fluorescence emitting material, a green fluorescence emitting material or a red fluorescence emitting material may be used.

Examples of a fluorenylamine compound according to the present invention will be illustrated below.

[Chem.4]

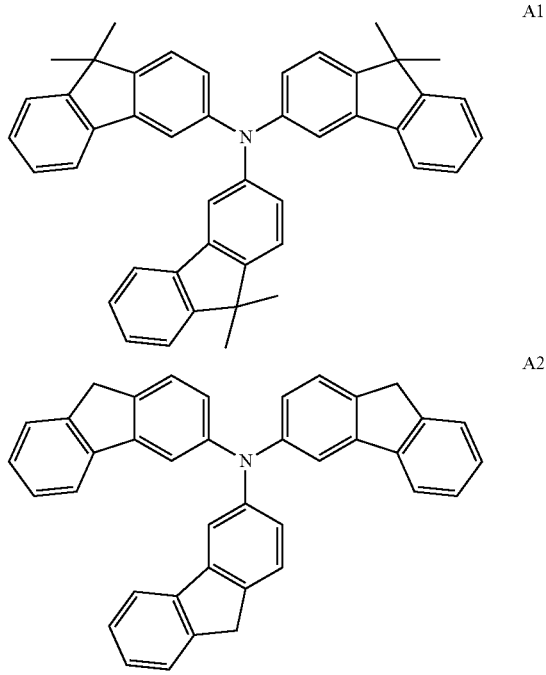

A3 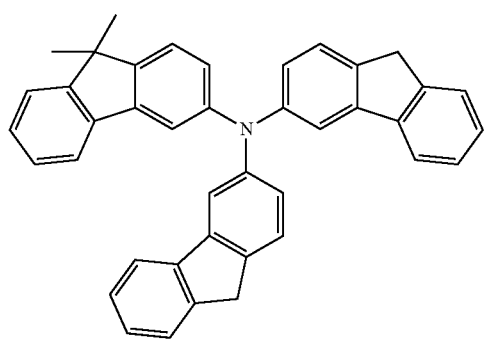

A4 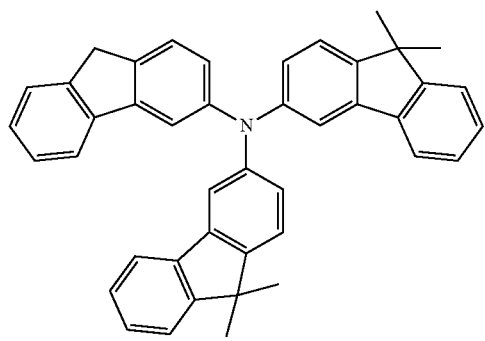

A5 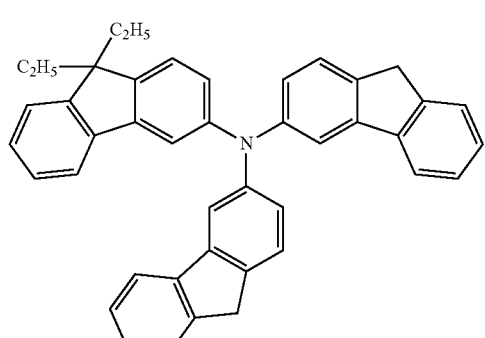

A6 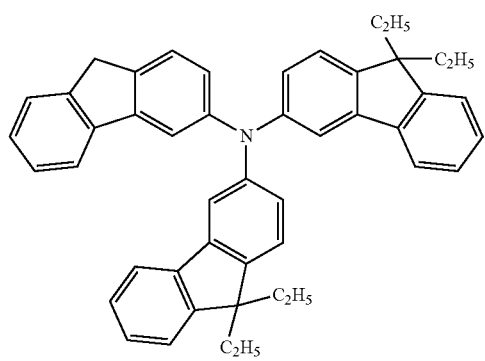

A7 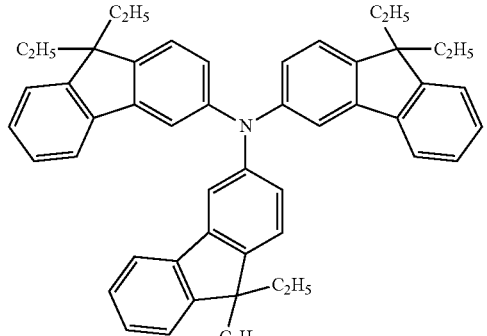

A8 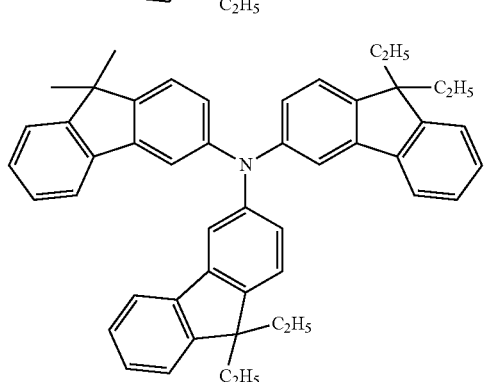

A9 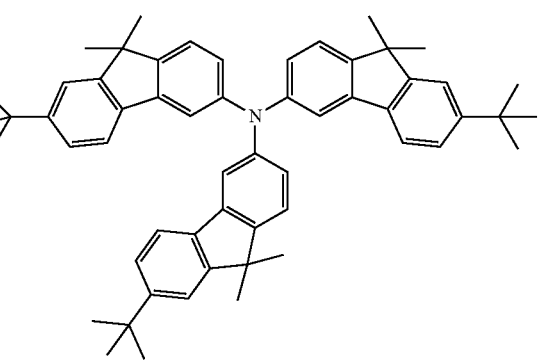

Hereinafter, an organic light emitting device according to the present invention will be described.

An organic light emitting device according to the present invention includes a pair of electrodes and an organic compound layer disposed between the pair of electrodes. The pair of electrodes are electrodes that have polarities opposite to each other, for example, a positive electrode and a negative electrode. An electric field in a forward direction in which the organic light emitting device emits light may be applied to the pair of electrodes. Alternatively, an electric field in a backward direction that is opposite to the forward direction may be applied to the pair of electrodes. The organic compound layer may be a single layer or a multilayer. The organic compound layer contains a fluorenylamine compound according to the present invention.

The multilayer may include layers appropriately selected from a hole injection layer, a hole transport layer, a light emitting layer, a hole and exciton blocking layer, an electron transport layer, an electron injection layer, and the like.

Since a fluorenylamine compound according to the present invention includes an arylamine, the fluorenylamine compound is excellent in terms of hole transport and is suitably provided in a light emitting layer or a hole transport layer disposed between a light emitting layer and a positive electrode in an organic light emitting device.

When a hole transport layer does not contain a fluorenylamine compound according to the present invention, for example, when a light emitting layer contains a fluorenylamine compound according to the present invention, examples of a compound contained in the hole transport layer include, but are not limited to, triarylamine derivatives, phenylenediamine derivatives, stilbene derivatives, phthalocyanine derivatives, porphyrin derivatives, poly(vinylcarbazole), poly(thiophene), and other conductive polymers.

When a light emitting layer does not contain a fluorenylamine compound according to the present invention, for example, when a hole transport layer contains a fluorenylamine compound according to the present invention, examples of the host material of the light emitting layer include, but are not limited to, condensed ring compounds (for example, fluorene derivatives, naphthalene derivatives, anthracene derivatives, pyrene derivatives, carbazole derivatives, quinoxaline derivatives, and quinoline derivatives); organic aluminum complexes such as tris(8-quinolinolate) aluminum; organic zinc complexes; triphenylamine derivatives; and polymer derivatives such as poly(fluorene) derivatives and poly(phenylene) derivatives.

When a fluorenylamine compound according to the present invention is the host material of a light emitting layer, examples of a guest material of the light emitting layer include, but are not limited to, condensed ring compounds (for example, fluorene derivatives, naphthalene derivatives, anthracene derivatives, pyrene derivatives, carbazole derivatives, quinoxaline derivatives, and quinoline derivatives); compounds in which such condensed ring compounds have been substituted with substituents such as amino groups; iridium complexes; and platinum complexes.

Examples of a compound for forming a hole injection layer disposed between a positive electrode and a hole transport layer include compounds such as copper phthalocyanine, triarylamine derivatives, fluorocarbon polymers, polyaniline, and polythiophene.

A fluorenylamine compound according to the present invention may be contained in both a hole transport layer and a light emitting layer of a single organic light emitting device.

Examples of a compound for forming an electron injection layer or an electron transport layer that is disposed between a light emitting layer and a negative electrode include, but are not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

A material used for forming a positive electrode has a high work function. Examples of such a material include, but are not limited to, elemental metals such as Au, Pt, Ag, Cu, Ni, Pd, Co, Se, V, and W; alloys of such metals; metal oxides such as ITO and IZO; and conductive polymers such as polyaniline, polypyrrole, and polythiophene. These electrode materials may be used alone or in combination. A positive electrode may have a single layer configuration or a multilayer configuration.

A material used for forming a negative electrode has a low work function. Examples of such a material include, but are not limited to, alkali metals such as Li; alkaline-earth metals such as Ca; elemental metals such as Al, Ti, Mn, Ag, Pb, and Cr; alloys of such elemental metals; and metal oxides such as ITO.

In an organic light emitting device according to the present invention, an organic compound layer may be formed by, for example, the following method.

The layer may be formed by vacuum deposition or by a solution application method in which a material is dissolved in an appropriate solvent, the resultant solution is applied to a predetermined position, and the applied solution is dried to remove the solvent.

Hereinafter, applications of an organic light emitting device according to the present invention will be described.

An organic light emitting device according to the present invention may be used for a display apparatus or a lighting apparatus. In addition, such an organic light emitting device may be used for, for example, an exposure light source of an image forming apparatus employing an electrophotographic technique or a backlight of a liquid crystal display apparatus.

A display apparatus includes an organic light emitting device according to the present invention in a display section. The display section includes a plurality of pixels. Such a pixel includes an organic light emitting device according to the present invention and a TFT device. The positive electrode or the negative electrode of the organic light emitting device is connected to the drain electrode or the source electrode of the TFT device. Such a display apparatus may be used as an image display apparatus for a PC or the like.

Alternatively, such a display apparatus may be used for a display section of an image pickup apparatus such as a digital camera or a digital video camera. Such an image pickup apparatus includes a display section and an image pickup section including an image pickup system such as a lens for picking up images. Such a display apparatus may be used not only for a display section of an image pickup apparatus but also for a display section of an inkjet printer.

Such a display apparatus may be an image input apparatus including an image input section configured to receive data from an area CCD, a linear CCD, a memory card, or the like. Such a display apparatus may serve as a display section and an operation panel of an image pickup apparatus or an inkjet printer. That is, the display apparatus may have an image output function of displaying images on the basis of image data input from the outside and an input function of receiving processing data for the images. Such a display apparatus may be used for a display section of a multifunction printer.

Hereinafter, a display apparatus including an organic light emitting device according to the present invention will be described.

FIG. 1 is a schematic sectional view illustrating an organic light emitting device according to the present invention and a TFT device serving as an example of a switching device that is configured to switch between the light-emitting state and non-light-emitting state of the organic light emitting device and is connected to the organic light emitting device. FIG. 1 illustrates two sets of the organic light emitting device and the TFT device. The structure of these devices will be described below in detail.

The display apparatus in FIG. 1 includes a substrate 1 composed of glass or the like and a vapor barrier film 2 that is disposed on the substrate 1 and is configured to protect the TFT devices or an organic compound layer. The display apparatus also includes a gate electrode 3 formed of a metal, a gate insulation film 4, and a semiconductor layer 5.

A TFT device 8 includes the semiconductor layer 5, a drain electrode 6, and a source electrode 7. An insulation film 9 is disposed over the TFT device 8. A positive electrode 11 of an organic EL device is connected to the source electrode 7 through a contact hole 10. Such a configuration is not limitative for a display apparatus and it will suffice that any one of the positive electrode and the negative electrode is connected to any one of the source electrode and the drain electrode of the TFT device.

In FIG. 1, an organic compound layer 12, which is a multilayer organic compound layer, is illustrated as a single layer. A first protective layer 14 and a second protective layer 15 for suppressing degradation of the organic light emitting devices are disposed on a negative electrode 13.

Use of a display apparatus including an organic light emitting device according to the present invention enables displaying of images with stability for a long period of time.

EXAMPLES

Hereinafter, the present invention will be more specifically described with reference to examples. However, the present invention is not restricted to these examples.

Example 1

Synthesis of Exemplified Compound A1

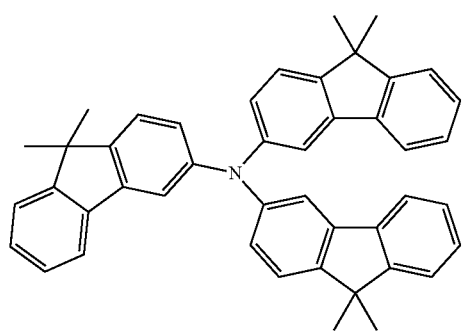

[Chem.5]

Exemplified compound A1 represented by this formula was synthesized in the following manner. A 100 ml three-neck flask was prepared and charged with 0.40 g (1.46 mmol) of 3-bromofluorene, 0.35 g (14.6 mmol) of lithium amide (product name: lithium amide, manufactured by KISHIDA CHEMICAL Co., Ltd.), 0.49 g (5.0 mmol) of sodium tertiary butoxide (product name: sodium tertiary butoxide, manufactured by TOKYO CHEMICAL INDUSTRY CO., LTD.); further, 20 ml of xylene; while the solution was stirred at room temperature in a nitrogen atmosphere, 0.5 ml (0.15 mmol) of tri-tertiary-butylphosphine (10 wt % hexane solution); and then 0.67 mg (0.153 mmol) of palladium dibenzylideneacetone (product name: palladium dibenzylideneacetone, manufactured by TOKYO CHEMICAL INDUSTRY CO., LTD.). The flask was purged with argon and then the solution in the flask was stirred to reflux for 6 hours. After the reaction was complete, an organic layer was washed with water, dried over anhydrous sodium sulfate, and then purified with a silica gel column (developing solvent mixture of heptane and toluene) to provide 0.14 g (yield: 50.0%) of Exemplified compound A1 (white crystals).

This compound was analyzed by MALDI-TOF MS (matrix assisted ionization time-of-flight mass spectrometry) and M+ of Exemplified compound A1, which is 593.0, was confirmed.

Exemplified compound A1 was subjected to $^1$H-NMR measurement with an ECA-400 manufactured by JEOL Ltd. (solvent: deuterochloroform) and the delta values (ppm) thereof were found to be 7.56 (2H, dt), 7.42 (1H, dd), 7.32-7.25 (3H, m), 7.10 (1H, dd), and 1.52 (6H, s).

The band gap of Exemplified compound A1 was determined from an ultraviolet-visible light absorption spectrum and it was found to be 3.02 eV. In this specification, each band gap was determined with a spectrophotometer U-3010 manufactured by Hitachi, Ltd. from absorption ends of a thin film formed on a glass substrate.

The ionization potential of Exemplified compound A1 was determined with an atmospheric photoelectron spectrometer (measurement apparatus name: AC-1, manufactured by Riken Keiki Co., Ltd.) and it was found to be 5.51 eV.

The Tg of Exemplified compound A1 was measured with a Pyris 1 (manufactured by PerkinElmer, Inc.) and it was found to be 154 degree (Celsius). Thus, Exemplified compound A1 had a high thermal stability.

Exemplified compound A1 was further evaluated in terms of amorphousness.

A chloroform solution of Exemplified compound A1 was prepared such that the concentration of Exemplified compound A1 was 0.1 wt %. This solution was dropped onto a glass substrate and spin-coating was performed to form a thin film. After that, the thin film was dried with a vacuum oven at 80 degree (Celsius) for 10 minutes to remove the solvent in the thin film.

The resultant substrate was left in the oven at 60 degree (Celsius) for a week. Then, the occurrence of crystallization in the film was visually inspected and it was confirmed that no crystallization occurred.

Synthetic Example

In EXAMPLE 1, by using the following bromo compounds instead of the 3-bromofluorene compound, the following Exemplified compounds can be synthesized.

| Chem. 6 | |
|---|---|
| Exemplified compound | Bromo compound |
| A4 | ![fluorene-Br] |
| A7 | ![diethylfluorene-Br] |
| A9 | ![dimethylfluorene-Br] |

Example 2

An organic light emitting device according to the present invention was produced by the following method.

A film of indium-tin oxide (ITO) was formed by a sputtering method on a glass substrate serving as a substrate so as to have a film thickness of 120 nm. Thus, a positive electrode was formed. This positive electrode was subjected to ultrasonic washing with acetone and then isopropyl alcohol (IPA) and then to boiling washing with IPA, and then dried. Furthermore, the positive electrode was subjected to UV and ozone cleaning.

A first hole transport layer was formed on the positive electrode in the following manner. A chloroform solution of Compound 3-1 illustrated below was prepared such that the concentration of Compound 3-1 was 0.1 wt %.

This solution was dropped onto the ITO electrode and spin-coating was performed initially at 500 RPM for 10 seconds and then 1,000 RPM for a minute. After that, the applied solution was dried in a vacuum oven at 80 degree (Celsius) for 10 minutes to remove the solvent in the thin film. Thus, the first hole transport layer having a thickness of 11 nm was formed.

Then, a second hole transport layer having a thickness of 20 nm was formed on the first hole transport layer by depositing Exemplified compound A1. In this deposition, film formation conditions used were a degree of vacuum of $1.0*10^{-4}$ Pa and a film formation rate of 0.1 nm/sec.

A light emitting layer having a thickness of 25 nm was then formed by codepositing Compound 3-3 (illustrated below) serving as a host material and Compound 3-2 (illustrated below) serving as a guest material such that the proportion of Compound 3-3 was 95 wt % and the proportion of Compound 3-2 was 5 wt %.

An electron transport layer having a thickness of 20 nm was then formed by depositing Compound 3-4 illustrated below. A metal layer film having a thickness of 0.5 nm was then formed of a deposition material composed of an aluminum-lithium alloy (concentration of lithium: 1 atom %) on the light emitting layer by a vacuum deposition method. Furthermore, an aluminum film having a thickness of 150 nm was formed by a vacuum deposition method. Thus, an organic light emitting device including the aluminum-lithium alloy film serving as a negative electrode was formed. In the deposition, film formation conditions used were a degree of vacuum of $1.0*10^{-4}$ Pa and a film formation rate of 1.0 to 1.2 nm/sec.

The thus-formed device was subjected to performance evaluation with a spectroradiometer SR-3 (manufactured by TOPCON CORPORATION). As a result, a blue light emission having a light emission efficiency of 3.23 cd/A and a light emission wavelength of 474.6 nm was observed under the applied voltage of 4.0 V.

When the current density of the device was held at 30 mA/cm$^2$ in a nitrogen atmosphere, the luminance of the device after a lapse of 100 hours was 85% of the initial luminance. Compounds 3-1 to 3-4 are illustrated below.

[Chem.7]

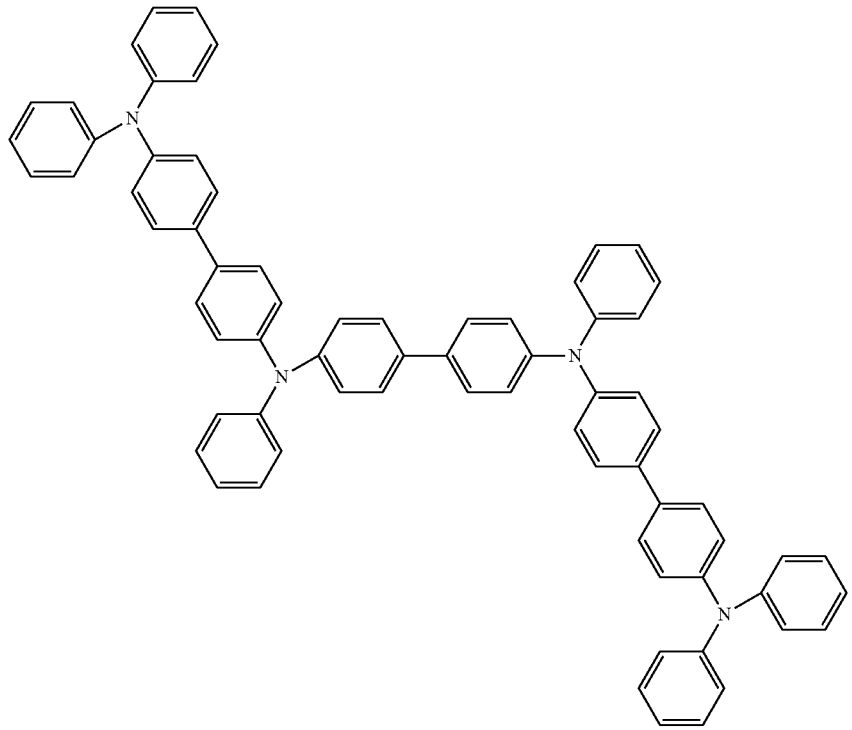

3-1

-continued 3-2

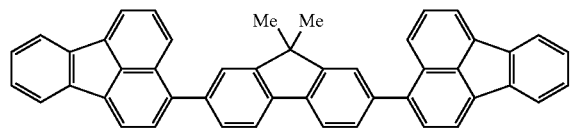

3-3

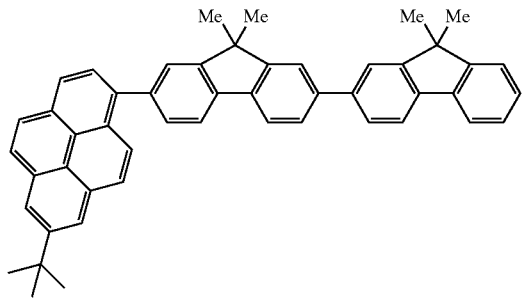

3-4

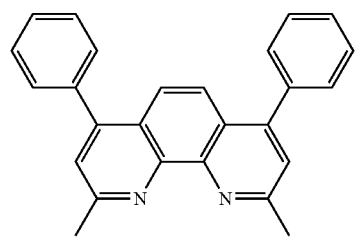

Example 3

An organic light emitting device in which a fluorenylamine compound according to the present invention was used as the host material of a light emitting layer was produced.

A film was formed of ITO by a sputtering method so as to have a thickness of 120 nm on a glass substrate serving as a substrate to prepare a positive electrode. This positive electrode was subjected to ultrasonic washing with acetone and then isopropyl alcohol (IPA) and then to boiling washing with IPA, then dried, and then UV and ozone cleaning.

A hole transport layer was formed on the positive electrode in the following manner. A chloroform solution of Compound 3-1 (illustrated above) was prepared such that the concentration of Compound 3-1 was 0.1 wt %.

This solution was dropped onto the ITO electrode and spin-coating was performed initially at 500 RPM for 10 seconds and then 1,000 RPM for a minute. After that, the applied solution was dried in a vacuum oven at 80 degree (Celsius) for 10 minutes to remove the solvent in the thin film. Thus, the hole transport layer was formed.

A light emitting layer having a thickness of 25 nm was then formed by codepositing Exemplified compound A1 serving as a host material and Compound 3-2 (illustrated above) serving as a guest material such that the proportion of Exemplified compound A1 was 95 wt % and the proportion of Compound 3-2 was 5 wt %. Furthermore, an electron transport layer and an Al electrode were formed as in EXAMPLE 2.

The thus-formed organic light emitting device was subjected to performance evaluation as in EXAMPLE 2. As a result, a good blue light emission having a light emission efficiency of 2.9 cd/A and a light emission wavelength of 475.0 nm was observed under the applied voltage of 4.0 V.

When the current density of the device was held at 30 mA/cm$^2$ in a nitrogen atmosphere, the luminance of the device after a lapse of 100 hours was 81% of the initial luminance.

In EXAMPLES 1 to 3, the compound in which each of $R_1$ to $R_6$ in the general formula is a methyl group was used. However, when the methyl group is substituted with any one of a hydrogen atom, an ethyl group, a n-propyl group, an isopropyl group, a n-butyl group, an isobutyl group, a sec-butyl group, and a tert-butyl group, similar advantages are provided.

This is because such a substituent enhances the degree of amorphousness of the compound without changing the electron state of the compound.

In EXAMPLES 1 to 3, the compound in which each of $R_{21}$ to $R_{23}$ in the general formula is a hydrogen atom was used. However, when the hydrogen atom is substituted with any one of a methyl group, an ethyl group, a n-propyl group, an isopropyl group, a n-butyl group, an isobutyl group, a sec-butyl group, and a tert-butyl group, similar advantages are provided. This is because such a substituent enhances the degree of amorphousness of the compound without changing the electron state of the compound.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-254006, filed Nov. 5, 2009, which is hereby incorporated by reference herein in its entirety.

The invention claimed is:

1. A fluorenylamine compound represented by a general formula below,

[Chem.2]

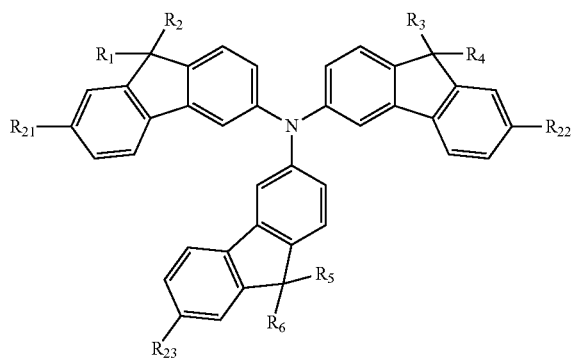

where $R_1$ to $R_6$ are each independently selected from a hydrogen atom and alkyl groups; $R_{21}$ to $R_{23}$ are each independently selected from a hydrogen atom and the alkyl groups; and the alkyl groups are a methyl group, an ethyl group, a n-propyl group, an isopropyl group, a n-butyl group, an isobutyl group, a sec-butyl group, and a tert-butyl group.

2. A material for an organic light emitting device, the material being the fluorenylamine compound according to claim 1.

3. An organic light emitting device comprising a pair of electrodes and an organic compound layer disposed between the pair of electrodes, wherein the organic compound layer contains the fluorenylamine compound according to claim 1.

4. The organic light emitting device according to claim 3, wherein the pair of electrodes are a positive electrode and a negative electrode; the organic compound layer is a hole transport layer; and the hole transport layer is disposed between a light emitting layer and the positive electrode.

5. The organic light emitting device according to claim 3, wherein the organic compound layer is a light emitting layer.

6. The organic light emitting device according to claim 4, wherein the light emitting layer contains a phosphorescence emitting material.

7. The organic light emitting device according to claim 5, wherein the light emitting layer contains a phosphorescence emitting material.

8. A display apparatus comprising a plurality of pixels, wherein the plurality of pixels include the organic light emitting device according to claim 3 and a switching device connected to the organic light emitting device.

9. An image input apparatus comprising a display section, an image input section for receiving an image, and a plurality of pixels, wherein the plurality of pixels include the organic light emitting device according to claim 3 and a switching device connected to the organic light emitting device.

10. A lighting apparatus comprising the organic light emitting device according to claim 3.

11. An image forming apparatus comprising an exposure light source, the exposure light source comprising the organic light emitting device according to claim 3.

* * * * *